United States Patent
Steinemann et al.

[11] Patent Number: 5,456,723
[45] Date of Patent: Oct. 10, 1995

[54] METALLIC IMPLANT ANCHORABLE TO BONE TISSUE FOR REPLACING A BROKEN OR DISEASED BONE

[75] Inventors: Samuel G. Steinemann, St. Sulpice, Switzerland; Lutz Claes, Ulm, Germany

[73] Assignee: Institut Straumann AG, Waldenburg, Switzerland

[21] Appl. No.: 931,643

[22] Filed: Aug. 17, 1992

Related U.S. Application Data

[63] Continuation-in-part of Ser. No. 839,006, Feb. 14, 1992, abandoned, which is a continuation of Ser. No. 433,683, Nov. 8, 1989, abandoned.

[30] Foreign Application Priority Data

Mar. 23, 1989 [CH] Switzerland ............... 1091/89

[51] Int. Cl.$^6$ ..................... A61F 2/28
[52] U.S. Cl. ................... 623/16; 606/76
[58] Field of Search ................. 623/10, 11, 16, 623/18, 22, 20; 427/2; 606/76

[56] References Cited

U.S. PATENT DOCUMENTS

| | | | |
|---|---|---|---|
| 3,664,888 | 5/1972 | Oga et al. ............................... | 148/6.27 |
| 4,406,761 | 9/1983 | Shimogori et al. ................... | 204/144.5 |
| 4,524,125 | 6/1985 | Huang .................................... | 430/302 |
| 4,629,464 | 12/1986 | Takata et al. ........................... | 623/16 |
| 4,702,930 | 10/1987 | Heide et al. ............................. | 623/16 |
| 4,704,126 | 11/1987 | Baswell et al. ......................... | 623/10 |
| 4,932,964 | 6/1990 | Bittmann et al. ........................ | 623/1 |
| 5,061,352 | 10/1991 | Kelly et al. ............................. | 204/129 |
| 5,156,723 | 10/1992 | Pliefhe et al. .......................... | 204/129.75 |
| 5,186,796 | 2/1993 | Kelly et al. ............................. | 204/129.35 |
| 5,219,361 | 6/1993 | von Recum et al. .................... | 623/11 |

FOREIGN PATENT DOCUMENTS

| | | | |
|---|---|---|---|
| 0455929 | 11/1991 | European Pat. Off. ................. | 623/21 |
| 1061811 | 12/1983 | U.S.S.R. ................................. | 623/20 |

OTHER PUBLICATIONS

Freed et al., Trans Am. Soc. Artif. Intern. Organs, vol. XXXI, 1985, pp. 230–232.
Wastie et al., Trans Am. Soc. Artif. Intern. Organs, vol. XXX, 1984, pp. 556–560.

*Primary Examiner*—David H. Willse
*Attorney, Agent, or Firm*—Anderson Kill Olick & Oshinsky

[57] ABSTRACT

The prevailing opinion, supported by observations, has been in the art, that any implant of titanium or of another similar material is to have a contact surface roughness of more than 20 μm to yield a good bond between bone and implant. The present invention is based upon the recognition, that the bond between bone and implant may be substantially improved by providing the contact surface of the implant with a micro-roughness of 2 μm or less. According to the method of the invention such micro-roughness can be readily produced by subjecting the contact surface to pickling in a reducing acid.

7 Claims, 3 Drawing Sheets

METALLIC IMPLANT ANCHORABLE TO BONE TISSUE FOR REPLACING A BROKEN OR DISEASED BONE

This is a 1.62 continuation-in-part application of Ser. No. 07/839,006, filed Feb. 14, 1992, abandoned which in turn is a 1.62 continuation of application of Ser. No. 07/433,683, filed Nov. 8, 1989, abandoned.

BACKGROUND OF THE INVENTION

1. Field of the Invention

The present invention refers to a metallic implant to be applied to a human or animal bone, the implant having a porous surface to come in contact with the bone and to intergrow therewith. Implants of this kind are used as prostheses in medicine, more specifically in orthopedics, for replacing broken or diseased bone, and in dentistry, for building artificial teeth. The implant must be made of a non-corrosive material and must be compatible with the surrounding tissue, meaning that it should not produce an immunologic reaction effecting rejection by the body. The invention also refers to a method of making the metallic implant.

In the following the term "surface" or "contact surface" shall be used to refer to the implant surface intended to be brought into contact with the bone to form an "interface" therewith, at which interface the bone will intergrow with the implant, forming a bond strong enough to resist all of the mechanical forces it will be subjected to while in use. This surface may be an inner or an outer surface, for example a cylindrical surface, depending upon the specific application and corresponding geometry of the implant.

2. Description of the Prior Art

Implants are known to be used in orthopedics and dentistry in various sizes and shapes. Among the larger ones are the prostheses used to replace the spherical element in the upper joint of the hip bone or femur, among the smaller ones are pins screwed into jaw bones for building artificial teeth. An implant of this kind is frequently made of one of the metals or elements titanium, zirconium, niobium or tantalum, or of a tissue-compatible alloy having one of the aforementioned elements as its main component. A common problem with such implants consists in the necessity of implementing the measures required for the bone substance to establish a speedy and lasting bond or connection with the contact surface of the implant. Other terms used in the art for this process include "implant anchoring" and "osseointegration".

With reference to bone implants, the following statements were made in the Abstract of a Study by the Work Committee for Implants of the German Society for Materials Testing, made public in Berlin on Nov. 17, 1987:

"Combined tension and histomorphometric tests have shown that smooth contact surfaces of titanium implants do not provide adequate interfaces that would resist tension forces. Contact surface roughnesses of more than 20 µm are required if a tension-resistant bone implant bond or connection is to be built. Uniform geometrical surface patterns as well as non-uniform porous designs are capable of improving the tension strength of the bone-titanium interface or bond, especially if additional sandblasting is applied."

It is customary nowadays to coat the contact surface of an implant with a titanium plasma coat, or to produce a surface roughness thereon by sandblasting or by threading said contact surface. Of common knowledge are both the drawbacks of the surfaces so treated and the fact that contact surface roughness of this kind is required for achieving adequate adhesion between bone and implant. Such drawbacks essentially consist in the fact, that the mechanically brittle plasma layer has a tendency to break or peel off, and in that the surfaces roughened by sandblasting become contaminated by the blasted grains, most often corundum. Attempts made to subsequently to clean the contact surface by means of a pickling or corrosive solution such as hydrofluoric acid plus nitric acid ($HF+HNO_3$) resulted in a substantially less perfect intergrowth of bone substance and implant, and weaker anchoring of the implant in the bone through its contact surface.

Terms used in this specification are generally based on definitions in METALS HANDBOOK, desk edition, by Boyer and Gall, American Society for Metals, Metals Park, Ohio, 1985. According to this text (pages 27.20–27.25), roughness, one of the four elements of surface texture, is the most commonly used surface parameter. Further, surface measuring devices generally indicate the roughness, but do not indicate the physical character of the surface and in effect, several surfaces can be quite different in appearance and still yield similar roughness values. Among roughness parameters are the maximum peak-to-valley height ($R_t$), which can be determined by a surface measuring device, and peak count ($P_c$), which is the number of peak/valley pairs per linear unit of surface and the reciprocal of which is roughness spacing (RS). Thus, $R_t$ concerns perpendicular distances, while RS concerns horizontal distances and together these parameters provide a more accurate picture of the surface texture than either parameter alone.

SUMMARY OF THE INVENTION

Hence from what has been said heretofore it should be apparent that the art is still in need of a metallic implant which is not associated with the aforementioned drawbacks and limitations of the state-of-the-art proposals.

It is therefore a primary object of the present invention to provide a novel metallic implant to be applied to a human or animal bone, which is not associated with the drawbacks and limitations of the prior art as heretofore discussed and which effectively and reliably fulfills an existing need in the art.

Another and more specific object of the present invention relates to a new and improved metallic implant enabled to form an interface with its mating bone, at which the bone will readily intergrow with the implant and will speedily form with it a bond that is strong and durable and capable of resisting all of the mechanical forces it will be exposed to during its use.

A further object of the invention relates to a metallic implant provided with a specific type of contact surface texture, to yield an improved bond between implant and bone, capable of fulfilling exacting requirements in regards to mechanical properties, durability and safety of operation.

Another object of the invention relates to an implant of the aforementioned kind in which the improved surface texture is formed directly in the metal mass on the outer periphery of the contact surface, rather than on a brittle plasma coating to be separately applied thereunto.

Yet another object of the invention relates to a method for making the implant, the method to be adapted to include steps for forming specific microroughness on the contact surface.

The foregoing and other objects are attained in accordance with one aspect of the invention by providing a metallic implant to be applied to a human or animal bone, the implant being provided with a porous surface which is to come in contact with the bone, wherein the contact surface is provided with micro-roughness having fine pitting superimposed thereon, such that the maximum peak-to-valley height $R_t$ of the micro-roughness is greater than 10 μm and the roughness spacing RS is less than 10 μm. This specific micro-roughness is realized according to the invention by a process comprising treating a metallic body destined to become the implant with a reducing acid which attacks the metallic body to produce the specific micro-roughness thereon. This reducing acid may be one of a group of acids including hydrochloric acid (HCl), hydrofluoric acid (HF), and an acid mixture consisting of hydrochloric acid (HCl) and sulfuric acid ($H_2SO_4$). The reducing acid is preferably made to exert its action on the implant in its boiling state.

The invention possesses several advantages as compared to the metallic implants known in the art. Actual tests performed on implants according to the invention showed that a porous contact surface on a metallic implant is able to meet the conditions required for making the mating bone intergrow with the implant along the contact surface and speedily form a strong and durable bond, provided that the contact surface displays a micro-roughness with pits of the order of magnitude of 2 μm or less. More preferably, according to the invention, the texture of the surface is defined by the maximum peak-to-valley height of the microroughness, $R_t$, and roughness spacing, RS. It has been found that $R_t$ must be greater than 10 μm and preferably 20 to 30 μm and that RS must be less than 10 μm, preferably 0.5 to 10 μm and more preferably 1 to 5 μm. The preferable mean value of RS is 2 μm, which also corresponds to the preferable mean diameter of the pits. Roughness spacing has been found to be more important than common roughness itself. The small value of roughness spacing indicates a heavily pitted surface having a very large surface area. The improvement in the mechanical properties of the bond was also considerable compared to a plasma-coated implant.

The improvements were unquestionably related to the main feature of the invention, namely, that the contact surface was provided with a micro-roughness having an $R_t$ greater than 10 μm and an RS less than 10 μm. This micro-roughness was produced by means of an acid treatment using a reducing acid. This operation alone produced the results desired by effectively pitting the surface of the metallic surface to be implanted. Sandblasting may be used, however, as a step preceding the reducing acid treatment. If this is done, the particles sandblasted onto the contact surface will subsequently be dissolved by the reducing acid and thus removed from the contact surface. This will help avoid the contamination by the blasted particles and produce a contact surface with a fine pitting superimposed upon a micro-roughness having an $R_t$ larger than 10 μm as impressed by the sandblasted grains. In this case too, however, the required contact surface structure turns out to be formed integral with the metal mass rather than merely a coating.

Some preferred features of specific embodiments are described in the following.

The implant may be made of any material, by preference a metal or an alloy, which is tissue-compatible, meaning that it does not cause an immunologic rejection reaction, and which satisfies other requirements, such as relating to mechanical properties. Metals commonly used as implants are titanium or titanium-based alloys. Other possibilities include zirconium, niobium and tantalum, and alloys based on these elements. The microroughness with pit sizes of 2 μm or less and having an RS of less than 10 μm may be applied directly onto the contact surface, or else be superimposed upon micro-roughness having an $R_t$ in excess of 10 μm or even in excess of 20 μm, produced for example by sandblasting. The reducing acids used for implementing the required micro-roughness could be, by preference, hydrochloric acid (HCl), hydrofluoric acid (HF), or a mixture consisting of hydrochloric acid (HCl) and sulfuric acid ($H_2SO_4$), but could just as well be another corrosive acid selected to suit the particular application. Also, the reducing acid is to act upon the contact surface preferably in its boiling state, the exact conditions for this action may however be otherwise set, depending upon the specific requirements of each individual case.

BRIEF DESCRIPTION OF THE DRAWINGS

The subject matter of the invention will now be explained by making reference to the appended drawing illustrating preferred embodiments. In the drawing

FIG. 4 is a set of six scanning electron microscope images of six differently treated surfaces of titanium screws, wherein each bar corresponds to 100 μm; VI is a surface according to the invention; III is a plasma treated surface of the art and the remaining are comparative surfaces.

DETAILED DESCRIPTION OF THE PREFERRED EMBODIMENTS

Tests were performed using six 4.5mm ×12mm long titanium screws (so-called bone screws) as implants. Before being implanted each of the six screws I to VI was subjected on its contact surface to its own specific treatment, as follows:

Example I (comparison)—Electropolishing

A titanium screw was subjected to electropolishing in a perchloric acid/acetic acid bath for 10 seconds, at a temperature of 15° C.

Example II (comparison)—Sandblasting and Oxidizing Acid

The titanium screw was sandblasted with fine corundum having a particle size of 0.1 mm for 0.5 min. The screw was then treated with a mixture of 4 parts of HF (50%), 20 parts of $HNO_3$ (60%) and 76 parts of water for a period of 1.5 minutes at room temperature.

Example III (comparison)—Plasma Coating

The titanium screw was treated by plasma spraying of Ti to a thickness of about 50 μm.

Example IV (comparison) Sandblasting and Oxidizing Acid

The titanium screw was treated in the same manner as in Example II, except that sandblasting was carried out with medium-fine corundum having a particle size of 0.12–0.25

Example V (comparison)—Sandblasting and Oxidizing Acid

The titanium screw was treated in the same manner as in Example II, except that sandblasting was carried out with rough corundum having a particle size of 0.25–0.50 mm.

Example VI (invention)—Sandblasting and Reducing Acid

The titanium screw was sandblasted with rough corundum having a particle size of 0.25–0.50 mm for 0.5 minute. Then the thus treated screw was dipped in a bath containing 10 parts of HCl (30%), 80 parts of $H_2SO_4$ (60 %) and 10 parts of water, at boiling temperature for 1 minute.

Figure 1:
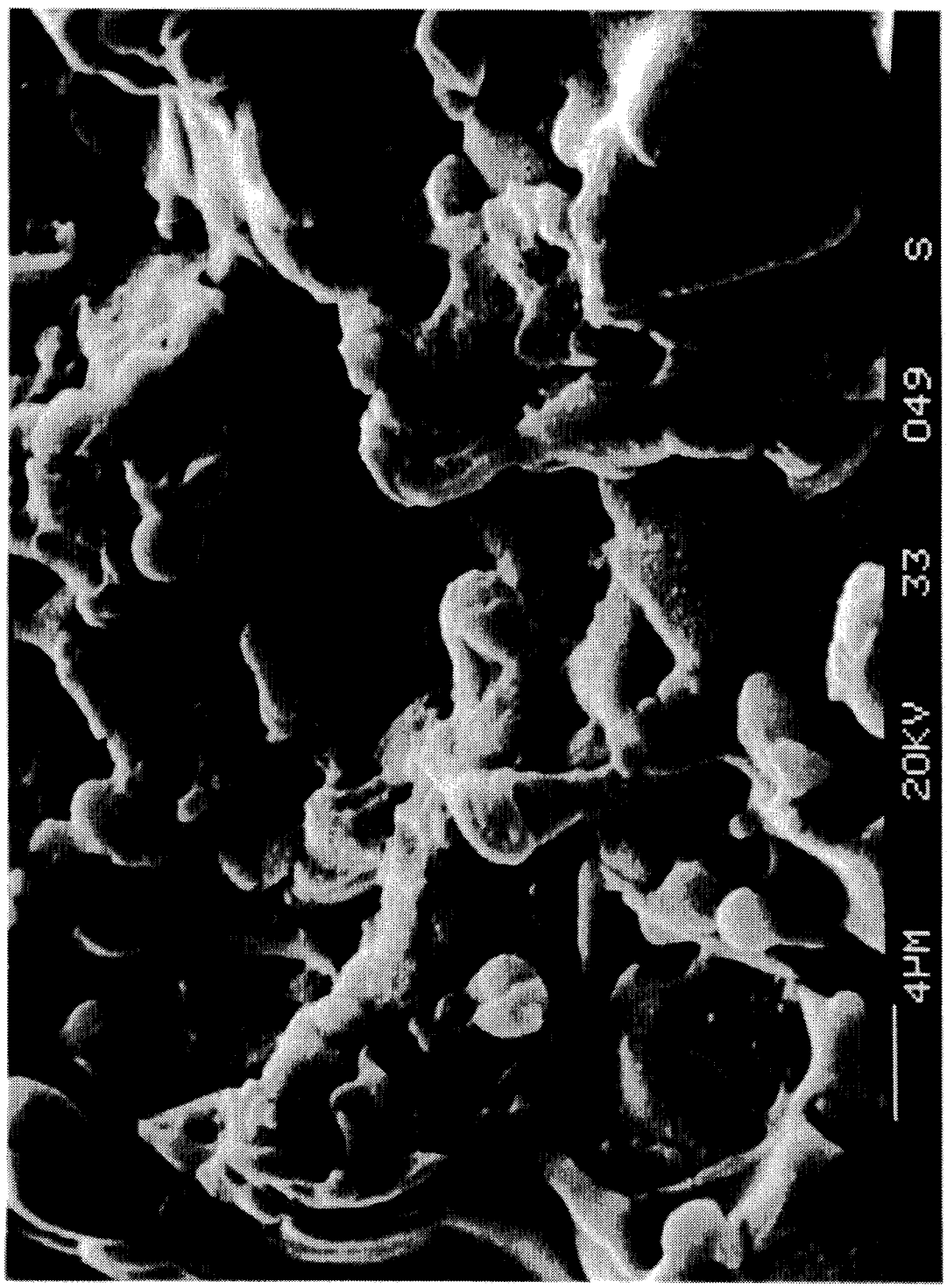
FIG. 1 is a image taken by means of an electron-microscope of the contact surface of a plasma-coated screw used as implant, at a magnification of 7500.
Figure 2:
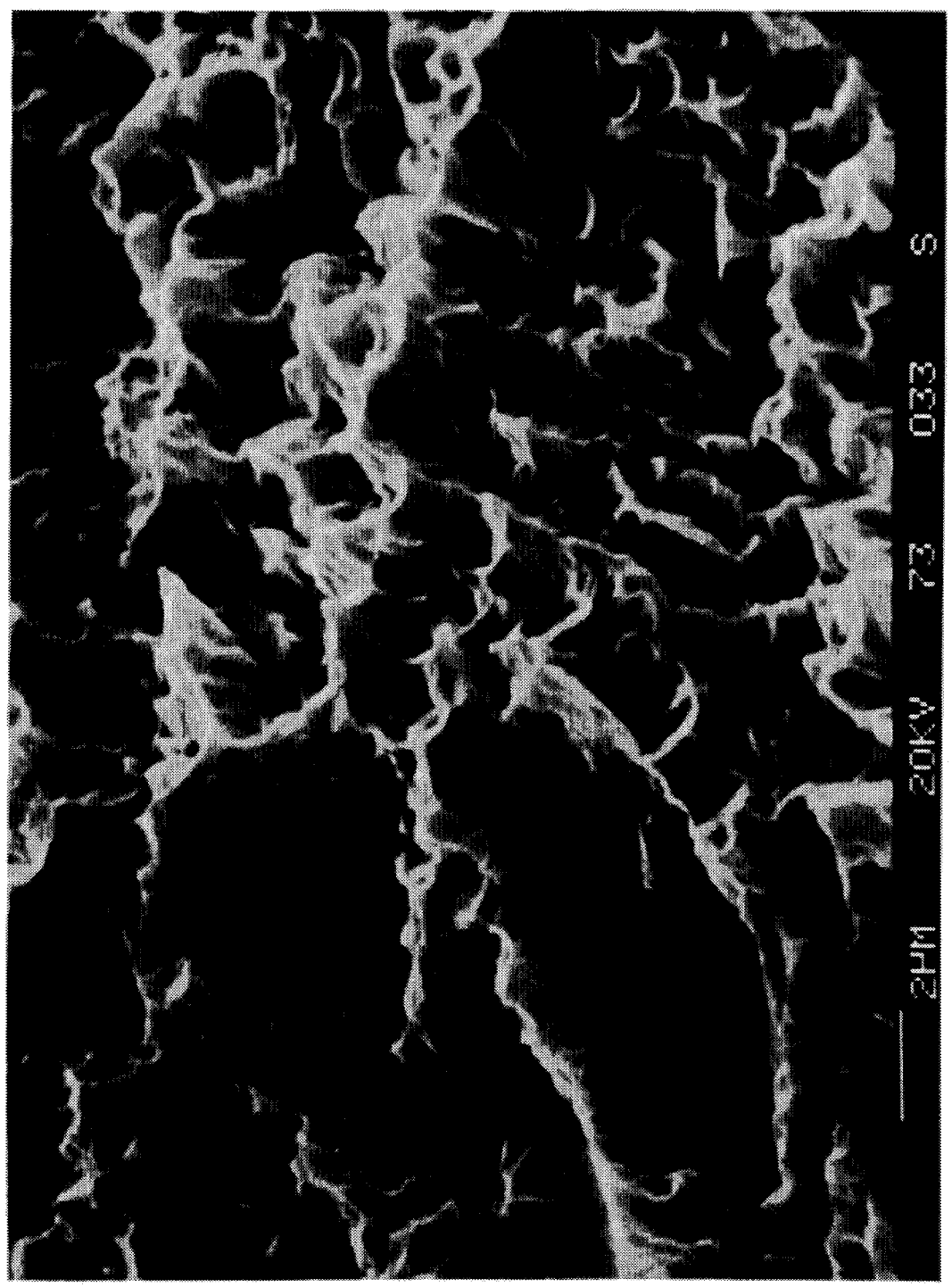
FIG. 2 is an image taken by the same means and magnification of the contact surface of another implant screw blasted with rough corundum (0.25–0.50 mm) and treated with HCl plus $H_2SO_4$ to implement the required microroughness, in accordance with the invention.

It has been found that bonding, or adhesion of bone to an implant depends on the texture of the contact surface. The surface texture of screws I–VI treated as set forth above was determined by roughness measurements and by the high-resolution scanning electromicroscope pictures shown in FIGS. 1, 2 and 4.

Roughness values were obtained by means of a standard mechanical-electronic device and the representative parameter is the maximum peak-to-valley height, $R_t$. In this connection it should be noted that In this connection it is to be remarked, that the resolution capacity of the roughness testing device was limited by the geometry of the diamond tip of the measuring probe. The diamond tip used had the following dimensions:

Cone angle: 85°

Radius of curvature at the tip: 5 μm A device of this kind is thus adequate for measuring roughness in general, but inadequate for measuring surface texture. Thus, $R_t$ gives dimensions perpendicular to the surface, but does not indicate the physical character of the surface. Another parameter, namely roughness spacing, is needed to specify dimensions parallel to the surface. To determine roughness spacing, the distance between peaks or pits is measured on the pictures made by the scanning electron microscope. Together, vertical peak-to-valley measurements of roughness, $R_t$, and horizontal measurements of roughness spacing, RS, are a measure of real, or effective contact surface. The results of these measurements are set forth in Table 1.

Figure 3:
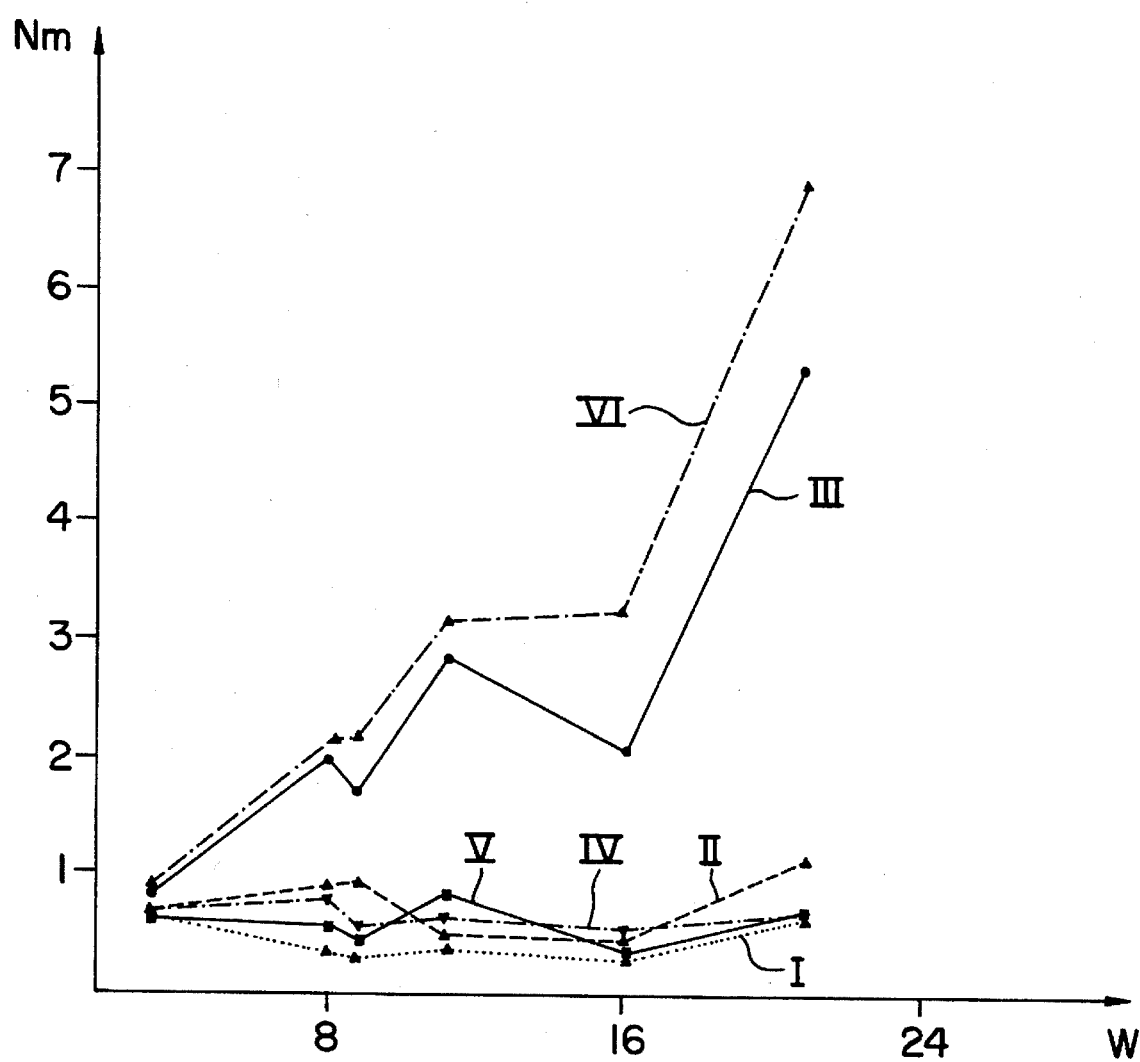
FIG. 3 is a graphic illustration of the results of tests relating to the improvement in quality of bonding of variously treated implant screws, expressed as changes in removing or loosening torque values (NM) as a function of number of weeks of allowed intergrowth between bone and contact surface, wherein VI illustrates bonding of an implant of the invention, III illustrates bonding of a plasma coated implant of the art and I, II and IV illustrate bonding of other comparative surfaces.

The screws were implanted into the tibia or shinbone of a test animal, specifically a sheep, applying a torque of 1 N.m. (Newton-meter). After a time interval of 3, 8 or 9 weeks and more, such as 11, 16 and 21 weeks, the torque required for removing the implanted screws from the bone was measured. The results plotted in FIG. 3 indicate that the screws subjected to the treatments I, II, IV and V failed to show any significantly improved adhesion to the bone compared to the adhesion observed after 3 weeks. In complete contrast thereto the test showed that the method of plasma coating of implants as used in the art promotes an intergrowth between bone and coat lasting longer, causing the quality of the bond to gradually improve at least till the end of the period of observation of 21 weeks. This result derived from systematic tests with a plasmacoated specimen is in good agreement with results obtained by other specialists in the field. As shown in Table 1 and FIG. 3, only screws which were plasma treated, as in Example III and treated in accordance with the invention, as in Example VI provide adequate bonding for a permanent implant.

TABLE 1

|  | $R_t$ | RS | Bonding |
|---|---|---|---|
| I | small, not det. | smooth | no |
| II | 10.3/9.0 | 15 | no |
| III | 76/41 | 5 | yes |
| IV | 7.7/6.3 | 20 | no |
| V | 20/21 | 18 | no |
| VI | 28/22 | 3 | yes | wherein, $R_t$ is maximum peak-to-valley height in μm
RS is roughness spacing in μm Completely new, unexpected and surprising were, however, the results obtained when providing the contact surface of the specimen with the micro-roughness produced by treatment with reducing acid as specified under VI: The anchoring effect or removing torque turned out to be as much as 7 times larger than the originally applied fastening torque, and not less than 30% larger than the removing torque obtained by the use of the plasma coat. Furthermore, the adhesion has been found to increase practically steadily and essentially with no interruption. This effect was unexpected, because it stands in perfect contrast to opinions expressed so far in literature. According to these opinions an optimum bond between bone and implant requires a contact surface roughness of more then 20 μm.

The presence of a micro-structure can also be checked by methods other than the scanning electron microscope. For example, a dark or black appearance of the contact surface indicates a micro-roughness smaller than the wave length of visible light, or else a wave length of the order of magnitude of visible light (about 0.5 μm). The implant screws pickled in reducing acid indeed showed black appearance.

Implants used in dental surgery are usually made of titanium or tantalum. These metals are corrosion resistant and behave inertly inside the living tissue, meaning that they elicit no rejection reactions. Similarly, zirconium and niobium are known to be tissue-compatible. Implants used in orthopedics must be made of metals having larger values of mechanical strength. Modern materials suitable for this purpose are described in CH-A-539-118. Preferred alloys therefor are, for example, Ti7Nb6A1, Ti5A12,5Fe, Ti15Mo7Zr3A1, whereby the numbers associated with the symbols express percentages by weight of the alloy components. All of these alloys can and have to be provided on their contact surfaces with the required micro-roughness by subjection to treatment in a reducing acid to form strong and durable bonds with their mating bones.

While there are shown and described present preferred embodiments of the invention, it is to be distinctly understood, that the invention is not limited thereto but may be otherwise variously embodied and practiced within the scope of the appended claims.

What is claimed is:

1. A metallic implant to be applied to a human or animal bone, comprising a porous metallic biocompatible surface, treated with a reducing acid to be provided with micro-roughness having a maximum peak-to-valley height $R_t$ greater than 10 μm and roughness spacing RS less than 10 μm, to come into contact with the bone and to intergrow therewith.

2. The metallic implant claimed in claim 1, wherein the $R_t$ of the micro-roughness is greater than 20 µm.

3. The metallic implant claimed in claim 1, wherein the $R_t$ of the micro-roughness is about 20 to 30 µm and the RS is about 1 to 5 µm.

4. The metallic implant claimed in claim 1, wherein the implant is composed of titanium metal or an alloy based on titanium.

5. The metallic implant claimed in claim 1, wherein the implant is composed of a metal selected from the group consisting of zirconium, niobium, tantalum or an alloy having zirconium, niobium or tantalum as its main component.

6. A metallic implant to be applied to a human or animal bone comprising a porous metallic biocompatible surface to come into contact with the bone and to intergrow therewith, wherein the contact surface is provided with micro-roughness and a fine pitting is superimposed on the micro-roughness so as to have a maximum peak-to-valley height $R_t$ greater than 10 µm and roughness spacing RS less than 10 µm.

7. The metallic implant claimed in claim 6, wherein the average diameter of the pits superimposed on the microroughness is 2 µm or less.

\* \* \* \* \*